(12) United States Patent
Berrevoets et al.

(10) Patent No.: US 6,413,260 B1
(45) Date of Patent: Jul. 2, 2002

(54) BONE CONNECTOR SYSTEM

(75) Inventors: Greg A. Berrevoets, Skandia; Francis J. Korhonen, Negaunee; Thomas S. Kilpela, Marquette, all of MI (US)

(73) Assignee: Pioneer Laboratories, Inc., Marquette, MI (US)

( * ) Notice: Subject to any disclaimer, the term of this patent is extended or adjusted under 35 U.S.C. 154(b) by 0 days.

(21) Appl. No.: 09/499,881

(22) Filed: Feb. 8, 2000

Related U.S. Application Data

(63) Continuation-in-part of application No. 09/375,330, filed on Aug. 17, 1999, now abandoned.

(51) Int. Cl.[7] ............................................. A61B 17/56
(52) U.S. Cl. ...................................................... 606/73
(58) Field of Search ............................. 606/73, 61, 53, 606/72, 75, 60; 411/389, 383

(56) References Cited

U.S. PATENT DOCUMENTS

| | | | | |
|---|---|---|---|---|
| 184,718 A | * | 11/1876 | Lewis ........................ 403/184 |
| 1,897,196 A | * | 2/1933 | Hunt .......................... 411/389 |
| 3,103,926 A | * | 9/1963 | Cochran et al. ............... 606/60 |
| 4,716,893 A | | 1/1988 | Fischer et al. ................. 128/92 |
| 5,334,184 A | | 8/1994 | Bimman ....................... 606/63 |
| 5,417,692 A | * | 5/1995 | Goble et al. ................... 606/73 |
| 5,513,989 A | | 5/1996 | Crisio ......................... 433/176 |
| 5,522,817 A | | 6/1996 | Sander et al. ................. 606/72 |
| 5,564,921 A | | 10/1996 | Marlin ........................ 433/172 |
| 5,667,510 A | | 9/1997 | Combs ........................ 606/86 |
| 5,827,285 A | * | 10/1998 | Bramlet ....................... 606/60 |
| 5,954,723 A | | 9/1999 | Sptezler ....................... 606/72 |
| 6,187,008 B1 | | 2/2001 | Hamman ...................... 606/72 |

* cited by examiner

Primary Examiner—David O. Reip
Assistant Examiner—(Jackie) Tan-Uyen T. Ho
(74) Attorney, Agent, or Firm—Fitch, Even, Tabin & Flannery

(57) ABSTRACT

A bone connector system comprises first and second connector members. At least one and preferably both of the connector members carries an external bone screw thread to permit securance within a bone. One of the connector members defines a sleeve having an outer end with longitudinal slots extending through the outer end, and a plurality of loops of an external screw thread positioned adjacent to the outer end. The other of the connector members defines a bore having a multiple loop, internal screw thread proportioned to engage the external thread when the connectors are brought together. Either or both of said connector members may define guidewire lumens.

26 Claims, 2 Drawing Sheets

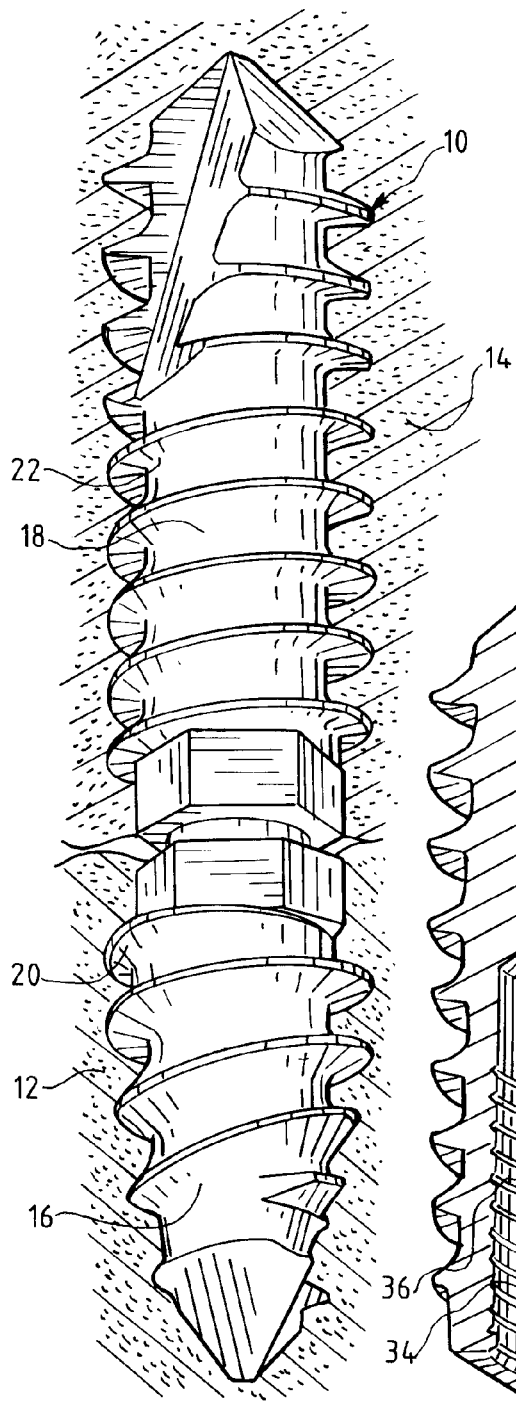
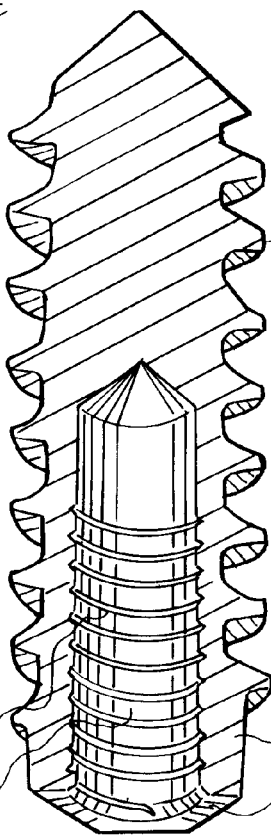
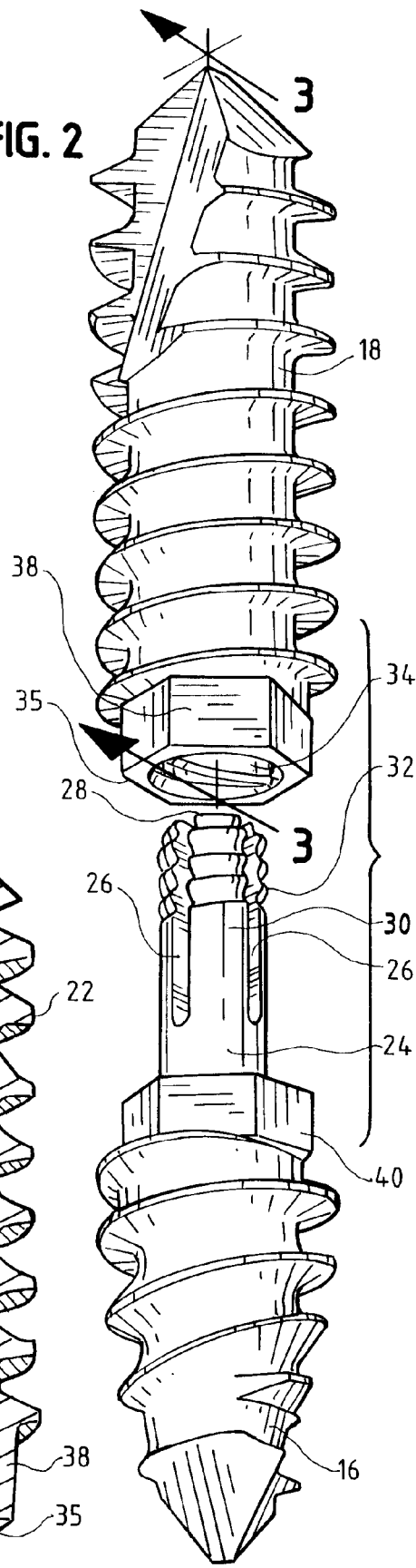
FIG. 1
FIG. 2
FIG. 3

BONE CONNECTOR SYSTEM

CROSS REFERENCE TO RELATED APPLICATION

This is a continuation-in-part of U.S. application Ser. No. 09/375,330, filed Aug. 17, 1999 now abandoned.

BACKGROUND OF THE INVENTION

In Goble et al. U.S. Pat. No. 5,417,692 a bone fixation and fusion system is disclosed, for example for the fusing of toe bones or the like together by firmly locking them in abutting relation to permit good healing. This is accomplished through the use of a male and female connector which, when bone fusion is the desired result, each have external bone threads so that each of the connectors may be driven into a separate bone.

The male connector is a solid, threaded body having a cross cut cylindrical sleeve with a split ring on the distal end. The female connector defines a cylindrical cavity having walls which may define spaced annular grooves or threads. The ring periphery on the distal end of the cylindrical sleeve 15 is intended to engage the grooves or threads in a somewhat resilient, spring-like manner resulting from the cross cut slots, for retention of the two connectors together.

It is of course desired for the two connectors to be retainable together in varying positions, to provide the best possible amount of fit between the bone fixation infusion system of the Goble et al. patent and the respective bones which carry them. In FIG. 9 of the Goble et al. patent the grooves 20b are shown to be provided in spaced relation, but there the spacing may be too wide to provide an optimum fit between the bones, i.e., the bones may be placed too near or too far from each other, because the best fit would be at a position between two of the grooves 20 or 20 b.

In FIG. 10 of Goble et al. "threads 21" are shown which are positioned more closely together than the grooves of FIG. 9. However, if the "threads" are true screw threads, then they are of helical shape, so that anything that would fit within the threads must be slightly angled away from perpendicular to the axis of the connectors. Accordingly, the split ring 18, 18a formed around the distal end of the cylindrical sleeve 15 described above will not fit well within helical threads, with the result that the retention of the two connectors may be more easily broken, and the connectors may separate in an undesirable, unplanned manner.

If the "threads 21" of Goble et al. are parallel, machined, annular grooves like the grooves 20b of FIG. 9, these are difficult to machine, particularly finely cut, closely spaced annular grooves of the size illustrated in FIG. 10, making the manufacture of the connector system of Goble et al. difficult.

By this invention, an improvement is provided in which a screw thread may be provided to both of the connectors, to be engaged in a well-fitting, solid connection which nevertheless is highly adjustable in its length. The screw threads which are used in this invention are easily machineable, to provide a lower cost, more reliable connection between the connectors of the bone connector system of this invention.

SUMMARY OF THE INVENTION

By this invention, a bone connector system is provided which comprises first and second connector members. At least one of the connector members carries an external bone screw thread to permit securance within a bone. In the circumstance where two bones are being connected together for fusing or the like, both of the connectors may carry external bone screw threads, to permit their separate securance within separate bones. Otherwise, one of the connector members may connect to an artificial tooth or another attachment to a bone.

One of the connector members defines a projection or boss having an outer end. Longitudinal slots extend through portions of the boss adjacent the outer end. The boss also carries a plurality of loops of an external screw thread adjacent to the outer end.

The other of the connector members define a bore for receiving the boss, having a multiple-loop, internal screw thread which is proportioned to engage the external thread of the boss when the connectors are brought together. Preferably, the multiple-loop internal thread has more loops than the external screw thread, so that the loops of the external screw threads can slide longitudinally along an array of loops of internal screw thread, and the respective threads may engage each other at a continuum of positions, so that the length of the bone connector comprising attached first and second connector members may be adjusted to the most desired fit along a series of very closely spaced, stepwise positions. The internal screw thread and the external screw thread may fit together with a multiple loop, close, tight fit without any mispositioning, as can be provided by a ring 18 as Gobel et al in extending perpendicular to the axis of the connector members when the ring is attempting to engage with a thread within the bore.

If desired, one or both connector members may define a central lumen, to permit a guidewire to extend through either or both connector members to facilitate placement thereof at a desired position in a bone. For example the connector member which does not define the boss may define a central lumen extending completely therethrough, being useable with the connector member having a boss and, with or without such a lumen.

DESCRIPTION OF THE DRAWINGS

In the drawings,

FIG. 1 is a perspective view of the bone connector system of this invention, shown in a position of implantation within and connecting two bones;

FIG. 2 is a perspective view showing the two separate connector members of the bone connector of FIG. 1;

FIG. 3 is a perspective view, taken in longitudinal section along line 3—3 of FIG. 2, of one of the connector members;

DESCRIPTION OF SPECIFIC EMBODIMENTS

Figure 4:
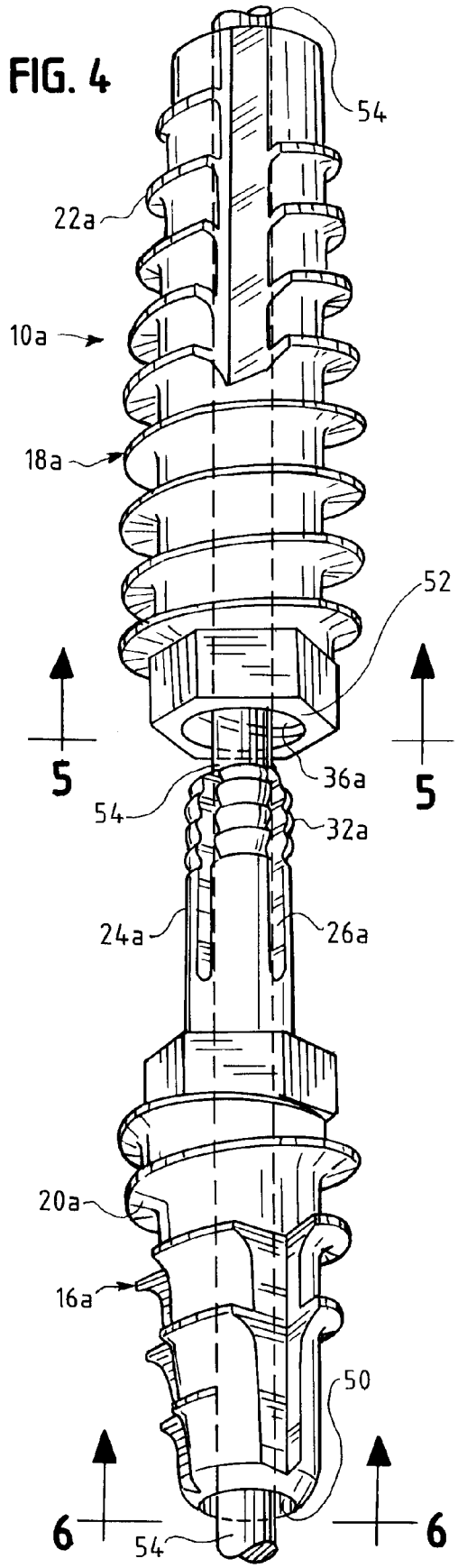
FIG. 4 is a perspective view showing two separate modified connector members which join together to form a bone connector similar in structure and function to the previous embodiment.

Referring to the drawings, bone connector system 10 is shown in FIG. 1 to be implanted between a pair of bones 12, 14, for example, a pair of bones in the toe which need fusion, and are so fused by the installation of the bone connector of this invention.

As also illustrated in FIG. 2, bone connector system 10 comprises a first connector member 16 and a second connector member 18. Each of connector members 16, 18 respectively carry external bone screw threads 20, 22 so that the respective connector members 16, 18 can be emplaced into respective, adjacent bones 12, 14 to secure the bones together. Besides toe bones, bones 12, 14 may, among others, comprise adjacent vertebra, finger bones, or any other adjacent bones which need to be fused together.

First connector member 16 also defines a projecting boss 24 having a plurality of longitudinal slots 26 extending through outer end 28 of boss 24. Typically, three or four slots 26 are present in boss 24, equidistantly distributed around the boss. In this embodiment, boss 24 has no central bore, although a bore may be provided if desired.

Both of connector members 16, 18 may be made of desirable surgically implantable metal. The respective intersecting slots 26 define between them in boss 24 a plurality of separate, longitudinally extending sections 30, which are somewhat flexible in the radial dimension.

Boss 24 also defines a plurality of loops, typically three as shown in FIG. 2, of an external screw thread 32, which screw thread is positioned adjacent to outer end 28 of boss 24.

Second connector member 18 defines a bore or lumen 34, open to the exterior at one end 35 thereof. Specifically, end 35 faces the first connector member 16. As shown in FIG. 3, lumen 34 has a wall that defines a multiple-loop, internal screw thread 36 which is proportioned to engage external screw thread 32 when the two connector members 16, 18 are brought together as shown specifically in FIG. 1. Thus, the two connectors may be connected by the insertion of boss 24 into bore 34 without relative rotation if desired, because of the radial springing characteristic of the respective boss sections 30 which are separated by slots 26. Sections 30 will be deflected inwardly as the first and second connector members 16, 18 are brought together, with sleeve 24 being inserted in bore 34. The respective threads 32, 36 may engage at any desired position along threads 36, so that the first and second connector members 16, 18 may assume a variety of retained positions where thread loops 32 engage various of the more numerous loops of thread 36 in a retentive manner, so that the overall length of bone connector 10 may be finely adjustable.

Each bone connector may carry an external, hexagonal section 38, 40 to permit bone screw threads 20, 22 of each connector member to be inserted into a respective bone 12, 14 by rotation with a wrench and action of the external bone screw threads 20, 22.

The first and second connector members of this invention are more easily machineable, while possessing the characteristic of multiple thread loop retention between the respective connector members 16, 18.

Figure 5:
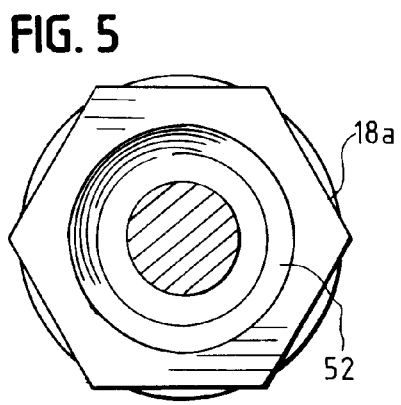
FIG. 5 is a sectional view taken along line 5—5 of FIG. 4.
Figure 6:
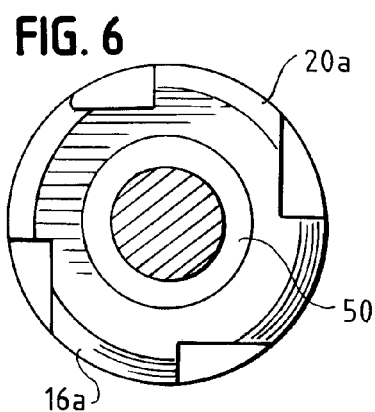
FIG. 6 is a sectional view taken along line 6—6 of FIG. 4.

Referring to FIGS. 4–6, an alternative design of bone connector system 10a is shown, comprising first connector member 16a and second connector member 18a, which are similar to the prior first and second connector members of the previous figures, with the exception that each of connector members 16a, 18a defines a respective central lumen 50, 52 extending through each of them, thus permitting first and second connector members 16a, 18a to be threaded onto a guidewire 54 to facilitate advancement and placement of the respective connector members 16a, 18a into their desired positions.

As in the previous embodiment, connector members 16a, 18a, respectively carry interrupted, external bone screw threads 20a, 22a so that the respective connector members can be emplaced into respective, adjacent bones to secure the bones together in the manner of the previous embodiment.

First connector member 16a also defines a projecting boss 24a which may be of identical design to the corresponding boss of the previous embodiment, having longitudinal slots 26a and external screw thread 32a.

Second connector member 18a defines lumen 52 as previously stated, extending completely through second connector member 18a while the lumen 34 in the previous embodiment only extends partially through the length of second connector member 18. Thus, as in the previous embodiment, a connection can be made between the internal screw threads 36a of second connector member 18a and the external interrupted screw threads 32a of first connector member 16a in a manner identical to the connection of the previous embodiment.

Thus, the connection advantages of the previous embodiment may be achieved, while at the same time, the connector members of this embodiment may be advanced along a guidewire. The respective screw threads 20a, 22a are capable of penetrating bone despite the presence of open ends at the opposed ends of the connected device 10a. If desired, a hole in the bone may be preformed to facilitate screw threaded advancement into the bone by each of the connector members 16a, 18a.

The above has been offered for illustrative purposes only, and is not intended to limit the scope of the invention of this application, which is as defined in the claims below.

That which is claimed:

1. A bone connector system which comprises first and second connector members, at least one of said connector members carrying an external bone screw thread to permit securance within a bone; one of said connector members defining a boss having an outer end, longitudinal slots extending through the boss adjacent said outer end, and a plurality of loops of an external helical screw thread adjacent to said boss outer end, the other of said connector members defining a bore having an internal helical screw thread proportioned to engage said external screw thread when the connectors are brought together.

2. The bone connector system of claim 1 in which both of said connector members carry external bone screw threads to respectively permit securance of said first and second connectors within different bones.

3. The bone connector system of claim 2 in which said internal screw thread has more loops than the external, helical screw thread.

4. The bone connector system of claim 3 in which said boss has three to four of said longitudinal slots.

5. The bone connector system of claim 1 in which said boss has three to four of said longitudinal slots.

6. The bone connector system of claim 5 in which said internal screw thread has more loops than the external, helical screw thread.

7. The bone connector system of claim 6 in which said internal screw thread has more loops than the external, helical screw thread.

8. The bone connector system of claim 1 in which at least one of said first and second connectors defines a lumen extending completely therethrough to permit guidewire advancement of said one connector.

9. The bone connector system of claim 8 in which both of said connector members carry external bone screw threads to respectively permit securance of said first and second connectors within different bones.

10. The bone connector system of claim 9 in which said internal screw thread has more loops than the external, helical screw thread.

11. The bone connector system of claim 10 in which said boss has three to four of said longitudinal slots.

12. A bone connector system which comprises first and second connector members, said connector members each carrying an external bone screw thread to permit securance within a bone; one of said connector members defining a boss having an outer end, longitudinal slots extending through the boss adjacent to said outer end, to define between them in said boss a plurality of separate, longitudinally extending sections which are somewhat flexible in the radial dimension, and a plurality of loops of an external, helical screw thread defined on said boss adjacent to said boss outer end, the other of said connector members defining a lumen extending completely therethrough, said lumen having a wall which defines a multiple-loop internal helical screw thread proportioned to engage said external screw thread when the connectors are brought together, to respectively permit securance of said first and second connectors within different bones.

13. The bone connector system of claim 12 in which said multiple-loop internal screw thread has more loops than the external screw thread of the boss.

14. The bone connector system of claim 13 in which said sleeve has three to four of said longitudinal slots.

15. The method of connecting together bones, which comprises:

inserting first and second connector members respectively into first and second bones;

inserting a portion of said first connector member into a bore of the other of said connector members, said portion of the first connector member having radial resilience and a plurality of loops of an external helical screw thread, and the second connector member having an internal helical screw thread proportioned to engage said external screw thread as the connectors are brought together, the advancement of said first connector member into the second connector member being substantially without relative rotation, whereby the internal and external helical screw threads advance across each other with resilient radial movement of the first connector member thread until the respective internal and external helical screw threads mate together in helical, retaining relationship at a desired position.

16. The method of claim 15 in which both of said connector members carry external bone screw threads for securance of said first and second connectors within different bones.

17. The method of claim 16 in which the radially resilient portion of said first connector is a boss having longitudinal slots extending therethrough to provide said resilience, and a plurality of loops of said external helical screw thread defined on said boss.

18. The method of claim 15 in which the radially resilient portion of said one connector is a boss having longitudinal slots extending therethrough to provide said resilience, and a plurality of loops of said external helical screw thread defined on said boss.

19. The bone connector system of claim 1 in which said first and second connector members may be connected together without relative rotation.

20. The bone connector system of claim 12 in which said first and second connector members may be connected together without relative rotation.

21. The bone connector system of claim 20 in which said bones are bone fragments.

22. The method of claim 15 in which said bones comprise bone fragments.

23. A bone connector system which comprises first and second connector members, at least one of said connector members carrying an external bone screw thread to permit securance within a bone, one of said connector members defining a boss having an outer end, said boss having a slot extending therethrough adjacent said outer end, and a plurality of loops of an external helical screw thread adjacent to said boss outer end, the other of said connector members defining a bore having an internal helical screw thread proportioned to engage said external screw thread when the connectors are brought together.

24. The bone connector system of claim 23 in which both of said connector members carry external bone screw threads to respectively permit securance of said first and second connectors within different bones, and in which said internal screw thread has more loops than the external helical screw thread with which it engages.

25. The bone connector system of claim 24 in which at least one of the first and second connectors defines a lumen extending completely therethrough to permit guide wire advancement of said one connector.

26. The bone connector system of claim 23 in which at least one of the first and second connectors defines a lumen extending completely therethrough to permit guide wire advancement of said one connector.

* * * * *